United States Patent [19]

Crews et al.

[11] 4,389,490

[45] Jun. 21, 1983

[54] METHOD OF STABILIZING PLATELETS FOR DETERMINING MULTIPLE PLATELET PARAMETERS IN REFERENCE CONTROL AND CALIBRATOR COMPOSITIONS; AND DILUENTS THEREOF

[75] Inventors: Harold R. Crews, Miami; James H. Carter, II, Ft. Lauderdale; Ted Sena, Miami, all of Fla.

[73] Assignee: Coulter Electronics, Inc., Hialeah, Fla.

[21] Appl. No.: 268,049

[22] Filed: May 29, 1981

[51] Int. Cl.³ .................. G01N 33/48; C09K 3/00
[52] U.S. Cl. .................................. 436/17; 436/10; 436/18
[58] Field of Search .............. 23/230 B; 252/408; 436/10, 17, 18

[56] References Cited

U.S. PATENT DOCUMENTS 3,912,450 10/1975 Boucher ........................... 252/408
3,968,248 7/1976 Boucher ........................... 252/408
4,102,810 7/1978 Armstrong ....................... 252/408
4,160,644 7/1979 Ryan ................................ 252/408
4,198,206 4/1980 Ryan ................................ 252/408
4,213,876 7/1980 Crews et al. .................... 252/408
4,219,440 8/1980 Runck et al. .................... 252/408
4,264,470 4/1981 Chastain, Jr. et al. .......... 252/408
4,299,726 11/1981 Crews et al. .................... 252/408
4,324,686 4/1982 Mundschenk ................... 252/408

FOREIGN PATENT DOCUMENTS 54-65095 5/1979 Japan ............................... 252/408

*Primary Examiner*—Teddy S. Gron

[57] ABSTRACT

Stabilized reference control and calibrator compositions for determining multiple platelet parameters in stand alone platelet controls and whole blood reference controls are prepared from platelets stabilized with a fixative-stabilizing composition containing glutaraldehyde and a non-ionic surfactant which is a mixture of ethoxylates of certain isomeric linear alcohols.

14 Claims, No Drawings

METHOD OF STABILIZING PLATELETS FOR DETERMINING MULTIPLE PLATELET PARAMETERS IN REFERENCE CONTROL AND CALIBRATOR COMPOSITIONS; AND DILUENTS THEREOF

BACKGROUND OF THE INVENTION

The introduction of new improved electronic counting devices has shown the need for improvement in quality control products, especially for human platelet reference controls for enumeration of cellular biological components for clinical diagnostic purposes. One such system is that of the Coulter ® S-Plus hematology system that counts and examines the volume distribution of human platelets in whole blood specimens. Instruments of similar type are sold by other manufacturers for this purpose.

Early examinations, utilizing the Coulter ® Channelyzer ® system for volume distribution analysis, revealed variations in size distributions of platelets from different human platelet rich plasma preparations. Shifts in the mode of the platelet distribution curves demonstrated count discrepancy. These observations raised questions as to their significance in clinical application.

Mean cell volume distribution analysis has gained recognition recently as a useful measurement for clinical application. Human platelet distribution width can now be calculated from specifically measured parameters. Each of these measured parameters lends itself to improvement in examining the log normal distribution of human platelets.

Specifications as to electronic calibration are well defined to the operator of such instruments. However, reference controls are needed to assure good quality control procedures and to monitor functional characteristics with respect to count modes and volume distribution analysis.

It is extremely important to adequately monitor these hematology systems. Any human platelet reference control must satisfy all the criteria that are measured on human patient specimens. The reference control must simulate as closely as possible that of normal fresh whole blood specimens. It must also conform to properly set thresholds as to the count mode, correctly balanced apertures, current, amplification gain settings, and responsiveness of the system as to all functional aspects.

Several reference control preparations are currently marketed; however, they lack long term stability as to count, mean cell volume, and size distribution. Also, changes and shifts in the mode result in erroneous counts. The common cause of count discrepancies is aggregation. Aggregation creates doublets that count in the white blood cell mode resulting in unreliable quality control measures. Still another discrepancy in count occurs due to poor performance of stability with time until the expected expiration date.

Attempts to stabilize human platelets have proved to be extremely difficult. One major problem is disintegration of the platelet membrane. When platelet membranes disintegrate, they cause debris which result in erroneous counts. New methods through improved computer technology for curve fitting of raw data are beset by these problems.

In U.S. Pat. No. 4,160,644 (1979), Ryan to Streck Laboratories, Inc., a method of preparing a reference control composition is described which is stable as to count and agitation in which a minor amount of solid polyethylene glycol, is added, either to a platelet suspension which has been fixed with glutaraldehyde, or to the diluent for this aldehyde treated platelet suspension, in order to achieve stabilization due to time and also during agitation. The preferred solid polyethylene glycol has a molecular weight of about 6000. It was reported that the lower molecular weight, liquid polyethylene glycols were ineffective for this purpose, even though the effect on the surface tension was similar. It was further reported in this patent that "an examination of the size of the surfactant treated platelets in a Coulter ® ZBI, an instrument which is used for size analysis of particles such as platelets and white blood cells, indicated that there was a large decrease in the size of the platelet. However, when platelets were examined under the microscope with an ocular-micrometer, no change in size of the platelet could be determined. The principle of the Coulter Counter ® is that it measures changes in conductivity; the surfactants alter the conductivity and thus make the platelet appear smaller to the instrument." The inventors of the present invention do not agree with this finding. They report that change in actual volume (due to shrinking) would not be distinguishable by use of a microscope which looks at diameter, because in a platelet-sized particle, a small change in diameter results in a large change in volume. They believe that the actual effect of surfactants is to cause a shape change, e.g., transition from discoidal to spherical, which changes apparent volume by a factor of 1:4.

In U.S. Pat. No. 4,198,206 to Ryan (1980), the aldehyde treated suspension is washed with a solution of (1) an amino acid which is glycine or alanine
(2) glycol, glycerol or methanol
(3) buffer salts
(4) a solid polyethylene glycol (molecular weight 4,000 to 20,000)

in order to produce platelets that do not aggregate, and that maintain their size for at least 6 months.

An aqueous solution of glutaraldehyde and non-ionic surfactant which is a mixture of ethoxylates of isomeric linear alcohols is described in U.S. Pat. No. 3,912,450 (1975) and U.S. Pat. No. 3,968,248 (1976), Boucher to Wave Energy Systems, Inc. These patents make no mention of the use of such a composition for hematological purposes, but only for sterilization.

A large family of analytes has been employed by other investigators to increase the rigidity by fixation of cellular membranes. Examples of these fixative agents are formaldehyde, glutaraldehyde, pyruvic aldehyde, and similar compounds. Use of such components may alter the size distribution and volume of human platelets. Aggregation of the platelets is an ever present problem, in addition to long term stability of the fixed platelets, limiting the usefulness of such compounds in improved quality control measures.

The present invention relates to a method of stabilizing human platelets which lends itself to eliminate these aforementioned discrepancies, so that the reporting of patient results to the diagnostic clinician can be assured of correct results, resulting in improved health care and improvements in the health care industry.

SUMMARY OF THE INVENTION

This invention relates to a method for stabilizing human or animal blood platelets for determining multiple platelet parameters in reference controls using electronic instrumentation. A platelet suspension is stabilized by adding to it a suitable quantity of glutaraldehyde and a non-ionic surfactant which is a mixture of ethoxylates of certain isomeric linear alcohols. The stabilized platelets can be utilized in stand alone platelet controls, as well as in whole blood human reference controls, to assure good quality control procedures and monitor functional characteristics with respect to count modes and volume distribution analysis.

DETAILED DESCRIPTION OF THE INVENTION

This invention relates to a method of stabilizing platelets for determining multiple platelet parameters in reference controls and calibrators for electronic particle counting instrumentation.

The method utilizes a composition which contains a combination of glutaraldehyde and a non-ionic surfactant which is a mixture of ethoxylates of isomeric linear alcohols having the formula:

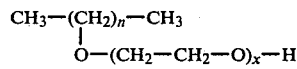

in which the polyoxyethylene chain is randomly attached to the linear aliphatic chain, $n=9$ to 13 and $x=9$ to 13, the composition being adjusted to predetermined pH and osmolality. The above described non-ionic surfactant is sold under the trademark Tergitol ® 15-S-12. The linear alkyl hydrophobic portion of the surfactant is a mixture of $C_{11}$ to $C_{15}$ linear chains. The hydrophylic portion is a polyoxyethylene chain of 9 to 13 oxyethylene groups randomly attached to the linear aliphatic chain through an ether linkage, as shown in the above formula.

Tergitol ® 15-S-12, which is manufactured by Union Carbide, has the following properties:
Molecular weight 728
Cloud point (1% aqueous solution) 90° C.
Pour Point 17° C.
Solubility in water at 25° C. 100%
Apparent specific gravity 20/20° C. 1.023
Density 8.49 lb/gal at 30° C.
Viscosity 48 cks at 40° C.
Flash Point 460° F. (ASTM method D 92)

The above described composition is used as a fixing and stabilizing agent in multiple analysis whole blood reference controls, and stand alone platelet controls and calibrators, in order to determine multiple platelet parameters, using electronic particle counting equipment.

Without being limited to any theory of action, a suggested mechanism for the stabilizing action is that native platelets in circulating plasma are in equilibrium with free and protein-bound calcium, certain protein clotting factors, and other antibodies found in human plasma. Collection of whole blood in conventional anticoagulants is generally believed to involve mainly the preferential chelation of active calcium, thus inhibiting the platelet-centered clotting mechanism. This can be demonstrated by the initiation of clotting after addition of supplemental calcium to the plasma. Clotting factors and coagulation proteins are apparently unaffected.

Upon addition of the stabilizing solution containing glutaraldehyde and surfactant to platelet rich plasma, the surfactant immediately begins binding to large proteins, lipids and cell membrane surfaces, modifying them into polar and less-polar regions. At the near neutral conditions of the protein bound surfactant solution, there is little or no electrical polarization induced into the protein molecules other than their native zwitterionic character at pH 7.2. Also at this pH, glutaraldehyde predominantly exists in the dimer form with very limited amounts of the active monomer in equilibrium. With no electrophilic centers induced, the rate of attack and reaction of active aldehyde on cellular and plasma proteins has been greatly reduced. Cross-linking reactions utilizing the second aldehyde group are even less favorable. This type of reaction is commonly referred to as "fixation" in that it permanently obscures the active hydrogen-bonding sites in the protein molecule, thus preventing conformational changes that occur in the thermal breakdown of plasma and cellular proteins.

The key to this entire process is the relative concentrations and nature of the particular surfactant used, glutaraldehyde, platelet and plasma proteins and the controlled pH conditions employed. Addition of more or stronger surfactants results in severe shape changes. Use of lower pH values or more glutaraldehyde results in significant cross-linking and resultant changing, thus interfering with count stability. The fact that this process does influence the integrity of the clotting factors has been demonstrated by recalcification and thrombin addition. Prothrombin times and activated partial thromboplastin times are infinite.

It has been suggested that when non-ionic surfactants are used, the non-ionic linear alcohol ethoxylates decrease the surface tension and increase the wettability at the platelet/liquid interface in such a manner that they promote a faster absorption rate of the glutaraldehyde molecules. This could also be the result of entrapping at the platelet liquid interface a higher concentration of glutaraldehyde molecules and/or a faster penetration inside the platelet particle.

We have now discovered that molecular weight of the specific surfactant has a direct effect upon the membrane properties. In addition to a reduction in the negative charge potential of the membrane, the surfactant reduces attraction of one cell to another, preventing aggregation or clumping. The molecular weight of the preferred liquid non-ionic surfactant, Tergitol ® 15-S-12 is below about 750. This contrasts with the high molecular weight of the solid polyethylene glycol (4,000 to 20,000) thought to be necessary by Ryan in U.S. Pat. Nos. 4,160,644 and 4,198,206.

Our invention produces long term stability sufficient to show the true relationship of all volume distribution functions expressed in examination of normal human platelets, including:
  A. Mean
  B. Mode
  C. Mean platelet volume
  D. Platelet distribution width
  E. Platelet count mode
  F. Signal/noise ratio.

This makes certain that the instrument can be properly examined with respect to all functions necessary to adequately examine human platelets, assuring that correct results can be reported to the diagnostic clinician.

It is an advantage of this invention that it can be used in the presence of urea and sodium chloride, the combination of which also has a stabilizing effect. The presence of both combinations of materials makes doubly sure that all parameters of the platelet control reagent will remain stable for any long period of time.

In a preferred embodiment of this invention, the first step is to centrifuge at slow speed fresh blood collected in a conventional anticoagulant to obtain a platelet rich plasma. Within two hours after phlebotomy, a solution of 50 ml of 2.0 molar aqueous solution of urea is added to the platelet rich media. Within five days after phlebotomy, 50 ml to 100 ml of the following fixative-stabilizing composition is added to each unit of the platelet rich media containing urea:

Fixative-Stabilizing Composition $NaH_2PO_4.H_2O$: 0.196 g
$Na_2HPO_4.7H_2O$: 1.960 g
$NaN_3$: 0.098 g
NaCl: 7.9 g
Glutaraldehyde, 49%: 8.4 g
Tergitol ® 15-S-12: 0.5 g
Water q.s.: 1 L Adjust to pH 7.3 to 7.4 with phosphates and to an osmolality of 290 mOs/kg with NaCl.

In the above fixative-stabilizing composition, the concentration of glutaraldehyde is about 0.1% to 5% w/v and the concentration of Tergitol ® 15-S-12 is about 0.01% to 1% w/v. The pH is adjusted to a range of 6.8 to 7.6 using phosphate, and the osmolality is adjusted to 280-340 milliosmoles per kilogram using sodium chloride.

The mixture is allowed to stand for 2 to 5 days at room temperature. The plasma and fixative-stabilizing composition is then expressed off to obtain the stabilized platelets.

For whole blood reference controls, the stabilized platelets are resuspended in 30 ml of 2 M urea, or in 30 ml of a conventionally manufactured whole blood control suspension media such as Coulter 4C ®, Baker Haem-C ®, or Dade CH-60 ®.

For stand alone platelet controls, the stabilized platelets are resuspended in 30 ml of 1:1 fixative-stabilizing composition and phosphate buffered saline solution, adjusted to pH 7.3 to 7.4 and 290 mOs/kg.

The fixative-stabilizing composition also can be added directly to the platelet rich plasma obtained by slow centrifrugation of fresh platelets to give stability of all useful platelet parameters. This contrasts with the two-step process of U.S. Pat. No. 4,160,644, in which a solid surfactant which is a polyethylene glycol having a molecular weight of 4,000 to 20,000, is first added to the aldehyde fixed platelet suspension and the diluent is mixed in thereafter; or the polyethylene glycol is first added to the diluent and the aldehyde fixed platelet suspension is added thereafter.

We claim:

1. A method of stabilizing platelets for determining multiple platelet parameters in reference controls and calibrators for electronic particle counting instruments which comprises adding to a platelet rich plasma a composition containing glutaraldehyde in a concentration of 0.1% to 5% w/v, and a non-ionic surfactant which is a mixture of ethoxylates of isomeric linear alcohols having the formula:

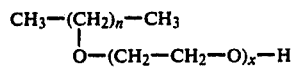

in which the polyoxyethylene chain is randomly attached to the linear aliphatic chain, n=9 to 13, and x=9 to 13, said nonionic surfactant being present in a concentration of 0.01 to 1% w/v, and the mixture being adjusted to a preselected range of pH and osmolality.

2. A method of stabilizing platelets for determining multiple platelet parameters in reference controls and calibrators for electronic particle counting instruments which comprises adding to a platelet rich plasma a composition containing glutaraldehyde in a concentration of 0.1% to 5% w/v, and a non-ionic surfactant which is a mixture of ethoxylates of isomeric linear alcohols having the formula:

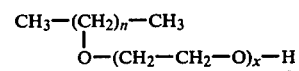

in which the polyoxyethylene chain is randomly attached to the linear aliphatic chain, n=9 to 13, and x=9 to 13, said nonionic surfactant being present in a concentration of 0.01% to 1% w/v and the mixture being adjusted to a pH of 7.3 to 7.4 and an osmolality of 290 mOs/kg.

3. A fixative-stabilizing composition for stabilizing platelets in platelet rich plasma containing 2.0 molar urea, comprising the following materials:

a. An aqueous solution of sodium chloride, a monobasic phosphate salt and a dibasic phosphate salt, adjusted to a selected pH and osmolality;

b. A bacteriostatic agent comprising sodium azide; and c. A nonionic surfactant which is a mixture of ethoxylates of isomeric linear alcohols having the formula:

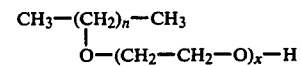

in which the polyoxyethylene chain is randomly attached to the linear aliphatic chain, n=9 to 13, and x=9 to 13 in a concentration of 0.01 to 1% w/v; and d. Glutaraldehyde in a concentration of 0.1% to 5% w/v.

4. A method for fixing and stabilizing platelets for use in whole blood controls or stand alone platelet controls which comprises:

A. Adding a 2.0 molar aqueous solution of urea to the platelets to be stabilized;

B. Within five days adding a fixative-stabilizing composition comprising a. an aqueous solution of sodium chloride, a monobasic phosphate salt and a dibasic phosphate salt, adjusted to a selected pH and osmolality;

b. a bacteriostatic agent comprising sodium azide; and c. a nonionic surfactant which is a mixture of ethoxylates of isomeric linear alcohols having the formula:

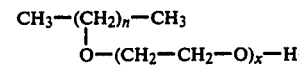

in which the polyoxyethylene chain is randomly attached to the linear aliphatic chain, n=9 to 13, and x=9 to 13, said surfactant being present in a concentration of 0.01 to 1% w/v; and d. Glutaraldehyde in a concentration of 0.1% to 5% w/v;

C. Allowing the mixture to stand for two to five days at room temperature; and

D. Expressing off the fixative-stabilizing composition, and then resuspending the stabilized platelets in a suspension media for determining multiple platelet parameters.

5. The method of claim 1 wherein the molecular weight of said non-ionic surfactant is below 750.

6. The method of claim 1 wherein said composition is adjusted to a pH in the range of 6.8 to 7.6.

7. The method of claim 1 wherein said composition is adjusted to an osmolality of 280 to 340 mOs/kg.

8. The composition of claim 3 wherein the molecular weight of said non-ionic surfactant is below 750.

9. The composition of claim 3 which is adjusted to a pH of 6.8 to 7.6.

10. The method of claim 4 wherein in step A said 2.0 molar urea is added to a platelet rich plasma.

11. The method of claim 4 wherein in step A said 2.0 molar urea is added to a platelet rich plasma which is harvested from blood of human or animal origin.

12. The method of claim 4 wherein in step A said platelets are saline washed human platelets.

13. The method of claim 4 wherein human platelets are added in Step A and the fixative stabilizing composition in Step B maintains the log normal distribution of said human platelets.

14. The method of claim 4 wherein in step D said suspension media is a whole blood control which contains red blood cells.

* * * * *